United States Patent
Niu et al.

(10) Patent No.: US 12,287,967 B2
(45) Date of Patent: Apr. 29, 2025

(54) METHODS AND SYSTEMS FOR INDEXING, CLASSIFYING, SEARCHING IMAGE DATA

(71) Applicant: WUHAN UNITED IMAGING LIFE SCIENCE INSTRUMENT CO., LTD., Hubei (CN)

(72) Inventors: Heying Niu, Wuhan (CN); Jiawei Lu, Wuhan (CN); Wenting Xu, Wuhan (CN); Yao Xing, Shanghai (CN)

(73) Assignee: WUHAN UNITED IMAGING LIFE SCIENCE INSTRUMENT CO., LTD., Wuhan (CN)

( * ) Notice: Subject to any disclaimer, the term of this patent is extended or adjusted under 35 U.S.C. 154(b) by 17 days.

(21) Appl. No.: 18/191,897

(22) Filed: Mar. 29, 2023

(65) Prior Publication Data
US 2023/0315289 A1 Oct. 5, 2023

(30) Foreign Application Priority Data
Mar. 31, 2022 (CN) .......................... 202210328997.8

(51) Int. Cl.
*G06F 3/06* (2006.01)
*G06T 11/00* (2006.01)

(52) U.S. Cl.
CPC .......... *G06F 3/0608* (2013.01); *G06F 3/0652* (2013.01); *G06F 3/0683* (2013.01); *G06T 11/003* (2013.01)

(58) Field of Classification Search
CPC .... G06F 3/0608; G06F 3/0652; G06F 3/0683; G06F 16/535; G06F 16/54; G06F 16/58; G06T 11/003; G16H 30/20
See application file for complete search history.

(56) References Cited

U.S. PATENT DOCUMENTS

| | | | | |
|---|---|---|---|---|
| 6,468,217 | B1* | 10/2002 | Fazioli | H04N 5/772 600/443 |
| 6,553,248 | B1* | 4/2003 | Gagnon | G01T 1/1647 600/407 |
| 2009/0083075 | A1* | 3/2009 | Henschke | G16H 10/60 705/3 |
| 2020/0167977 | A1* | 5/2020 | Lee | G06T 7/20 |
| 2020/0272324 | A1* | 8/2020 | Chanda | G06F 3/04883 |
| 2021/0303717 | A1* | 9/2021 | Neves | G06F 21/32 |

(Continued)

FOREIGN PATENT DOCUMENTS

| | | |
|---|---|---|
| CN | 104217447 A | 12/2014 |
| CN | 104407540 A | 3/2015 |
| CN | 110209506 A | 9/2019 |

(Continued)

*Primary Examiner* — Tasnima Matin
(74) *Attorney, Agent, or Firm* — METIS IP LLC

(57) ABSTRACT

Systems and methods for image data management are provided. The methods may include by running a first process, storing raw data collected in a scan of a subject into first storage space of the at least one storage device, and generating first information relating to the raw data. The methods may include by running a second process, obtaining the first information from the first process and storing the first information into second storage space of the at least one storage device. The methods may further include reconstructing the raw data into a reconstruction image of the subject based on the first information.

20 Claims, 8 Drawing Sheets

(56) References Cited

U.S. PATENT DOCUMENTS

2023/0006691 A1* 1/2023 Sloane ................ H03M 7/6011
2023/0315289 A1* 10/2023 Niu ...................... G06F 3/0608
                                                            711/100

FOREIGN PATENT DOCUMENTS

CN          113689518 A     11/2021
WO    WO-2023039736 A1 *    3/2023

* cited by examiner

METHODS AND SYSTEMS FOR INDEXING, CLASSIFYING, SEARCHING IMAGE DATA

This application claims priority to Chinese Patent Application No. 202210328997.8 filed on Mar. 31, 2022, the entire contents of which are hereby incorporated by reference.

TECHNICAL FIELD

The present disclosure generally relates to data management, and more particularly, relates to methods and systems for managing image data associated with a scan of a subject.

BACKGROUND

In preclinical life science research, a subject may be scanned using an imaging device such as a micro computed tomography (CT) device to obtain image data of the subject. According to the image data of the subject, information of tissues (e.g., lesions) and/or organs of the subject may be obtained, which can provide strong support for the life science research. The image data may include raw data, images in various formats (e.g., digital imaging and communications in medicine (DICOM)), and information recorded in a database associated with the imaging device, etc. The raw data refers to unreconstructed data collected by a detector of the imaging device. A reconstruction image may be generated through reconstruction of the raw data. Generally, the image data (e.g., raw data and reconstructed images) generated by a single scan of the imaging device may be 200-300 GByte. Due to a relatively large amount of data, the storage of the image data requires a lot of resources, and the consistency between the raw data and the reconstruction image may be difficult to maintain. Therefore, it is desirable to provide methods and systems for image data management with improved accuracy and efficiency.

SUMMARY

An aspect of the present disclosure relates to a method for image data management. The method may be implemented on a computing device including at least one processor and at least one storage device. The method may include by running a first process, storing raw data collected in a scan of a subject into first storage space of the at least one storage device; and generating first information relating to the raw data. The method may include by running a second process, obtaining the first information from the first process; and storing the first information into second storage space of the at least one storage device. The method may further include reconstructing the raw data into a reconstruction image of the subject based on the first information.

In some embodiments, the reconstructing the raw data into a reconstruction image of the subject based on the first information may include by running the second process, retrieving the raw data from the first storage space based on the first information; reconstructing the retrieved raw data into the reconstruction image of the subject; storing the reconstruction image of the subject into third storage space of the at least one storage device; generating second information relating to the reconstruction image; and storing the second information into the second storage space of the at least one storage device.

In some embodiments, the reconstructing the raw data into a reconstruction image of the subject based on the first information may include by performing a third process, obtaining the first information from the second process; retrieving the raw data from the first storage space based on the first information; and reconstructing the retrieved raw data into the reconstruction image of the subject.

In some embodiments, the method may further include by performing the third process, storing the reconstruction image of the subject into third storage space of the at least one storage device; and generating second information relating to the reconstruction image; and by running the second process, obtaining the second information from the third process; and storing the second information.

In some embodiments, the storing the second information may include updating the first information in the second storage space based on the second information.

In some embodiments, before storing the raw data collected in the scan of the subject into the first storage space, the method may further include determining whether the first storage space satisfies a condition; in response to determining that the first storage space does not satisfy the condition, determining at least one target raw data set from historical raw data sets that have already been stored in the first storage space; and deleting or compressing the at least one target raw data set stored in the first storage space.

In some embodiments, the determining the at least one target raw data set from historical raw data sets that have already been stored in the first storage space may include for each historical raw data set, constructing a feature vector representing the historical raw data set; and determining an evaluation score of the historical raw data set by inputting the feature vector into a machine learning model; and determining the at least one target raw data set from the historical raw data sets based on the evaluation score of each historical raw data set.

In some embodiments, the method may further include obtaining a deletion instruction to delete the reconstruction image and the corresponding raw data; and in response to the deletion instruction, deleting the raw data and the reconstruction image.

In some embodiments, the method may further include by running the first process, obtaining a protection instruction for protecting the raw data from deletion or compression; and in response to the protection instruction, copying the raw data into storage space other than the first storage space for permanent storage.

In some embodiments, the method may further include obtaining an association instruction with respect to the raw data; and in response to the association instruction, associating the raw data and other data relating to the raw data stored in the first storage space based on tag information of the raw data and the other data.

In some embodiments, the raw data includes raw data subsets collected by a plurality of acquisition modules of an imaging device, the method may further include by running the first process, determining whether each of the plurality of acquisition modules operates normally during data acquisition; and in response to determining that at least one of the plurality of acquisition modules does not operate normally during the data acquisition, deleting the raw data stored in the first storage space.

In some embodiments, the method may further include displaying a protection status of whether a set of raw data is protected on a user interface.

A further aspect of the present disclosure relates to an imaging system. The system may include an imaging device configured to scan a subject. The system may further include at least one storage device including a set of instructions and at least one processor in communication with the at least one storage device. When executing the set of instructions, the at least one processor may be directed to cause the system to implement operations. The operations may include by running a first process, storing raw data collected in the scan of the subject into first storage space of the at least one storage device; and generating first information relating to the raw data. The operations may include by running a second process, obtaining the first information from the first process; and storing the first information into second storage space of the at least one storage device. The operations may further include reconstructing the raw data into a reconstruction image of the subject based on the first information.

A still further aspect of the present disclosure relates to a non-transitory computer readable medium including executable instructions. When the executable instructions are executed by at least one processor, the executable instructions may direct the at least one processor to perform a method. The method may include by running a first process, storing raw data collected in a scan of a subject into first storage space of the at least one storage device; and generating first information relating to the raw data. The method may include by running a second process, obtaining the first information from the first process; and storing the first information into second storage space of the at least one storage device. The method may further include reconstructing the raw data into a reconstruction image of the subject based on the first information.

Additional features may be set forth in part in the description which follows, and in part may become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
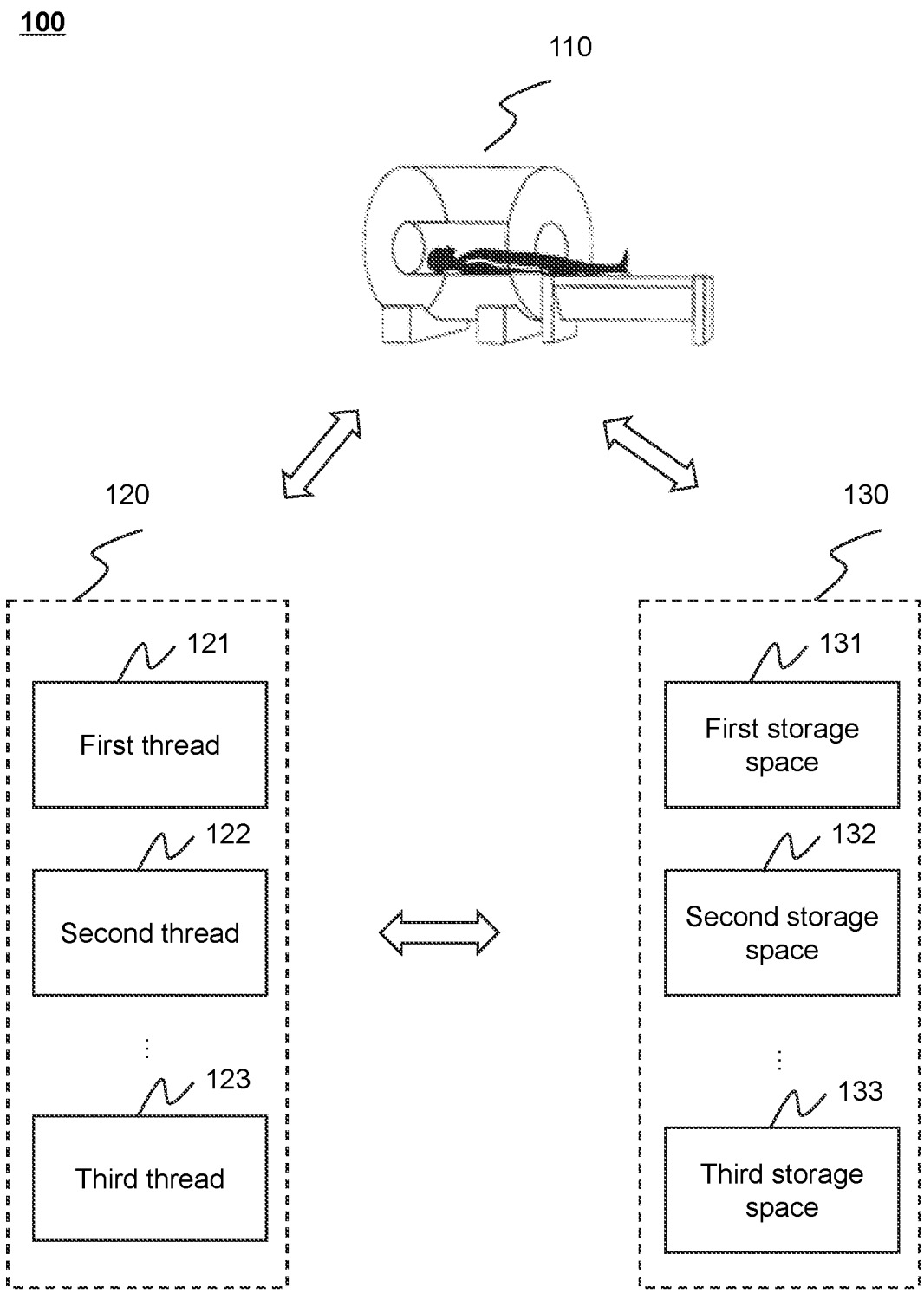
FIG. 1 is a schematic diagram illustrating an exemplary image data management system according to some embodiments of the present disclosure.

In the following detailed description, numerous specific details may be set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments may be readily apparent to those skilled in the art, and the general principles defined herein may be applied to other embodiments and applications without departing from the spirit and scope of the present disclosure. Thus, the present disclosure may be not limited to the embodiments shown, but to be accorded the widest scope consistent with the claims.

The terminology used herein may be for the purpose of describing particular example embodiments only and may be not intended to be limiting. As used herein, the singular forms "a," "an," and "the" may be intended to include the plural forms as well, unless the context clearly indicates otherwise. It may be understood that the terms "system," "unit," "module," and/or "block" used herein are one method to distinguish different components, elements, parts, sections or assemblies of different levels in ascending order. However, the terms may be displaced by another expression if they achieve the same purpose.

The modules (or units, blocks, units) described in the present disclosure may be implemented as software and/or hardware modules and may be stored in any type of non-transitory computer-readable medium or other storage devices. In some embodiments, a software module may be compiled and linked into an executable program. It may be appreciated that software modules may be callable from other modules or from themselves, and/or may be invoked in response to detected events or interrupts. Software modules configured for execution on computing devices may be provided on a computer readable medium or as a digital download (and can be originally stored in a compressed or installable format that requires installation, decompression, or decryption prior to execution). Such software code may be stored, partially or fully, on a memory device of the executing computing device, for execution by the computing device. Software instructions may be embedded in a firmware, such as an EPROM. It may be further appreciated that hardware modules (e.g., circuits) may be included in connected or coupled logic units, such as gates and flip-flops, and/or may be included in programmable units, such as programmable gate arrays or processors. The modules or computing device functionality described herein may be preferably implemented as hardware modules, but may be software modules as well. In general, the modules described herein refer to logical modules that may be combined with other modules or divided into units despite their physical organization or storage.

Certain terminology has been used to describe embodiments of the present disclosure. For example, the terms "one embodiment," "an embodiment," and/or "some embodiments" may mean that a particular feature, structure or characteristic described in connection with the embodiment is in at least one embodiment of the present disclosure. Therefore, it is emphasized and should be appreciated that two or more references to "an embodiment" or "one embodiment" or "an alternative embodiment" in various portions of this specification may not necessarily all referring to the same embodiment. Furthermore, the particular features, structures or characteristics may be combined as suitable in one or more embodiments of the present disclosure.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings may be for the purpose of illustration and description only and may be not intended to limit the scope of the present disclosure.

The flowcharts used in the present disclosure may illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Image data may include raw data and a reconstruction image. The raw data may refer to data obtained by scanning a subject using an imaging device such as a computed tomography (CT) device, a positron emission computed tomography (PET) device, etc. The reconstruction image may refer to an image obtained by reconstructing the raw data. Generally, the raw data and the reconstruction image may be managed using a same process of a device (e.g., a processing device, the imaging device). For example, the CT device may need a relatively long time to store a large amount of collected raw data, reconstruct the raw data to generate the reconstruction image, and store the reconstruction image, which increases resource occupation of the CT device and reduce data processing efficiency of the CT device.

Therefore, the present disclosure provides methods and systems for image data management implemented on a computing device including at least one processor and at least one storage device. The methods may include storing raw data collected in a scan of a subject into first storage space of the at least one storage device and generating first information relating to the raw data. The storage of the raw data and the generation of the first information may be implemented by running a first process. The method may further include obtaining the first information from the first process; storing the first information into second storage space of the at least one storage device; and reconstructing the raw data into a reconstruction image of the subject based on the first information stored in the second storage space. The obtaining of the first information, the storage of the first information, and the reconstruction of the raw data may be implemented by running a second process. According to the method of the present disclosure, the raw data and the reconstruction image may be managed through different processes, which decouples the management of the raw data and the management of the reconstruction image, thereby improving the management efficiency of the image data.

FIG. 1 is a schematic diagram illustrating an exemplary image data management system according to some embodiments of the present disclosure. As illustrated in FIG. 1, the image data management system 100 may include an imaging device 110, a processing device 120, and a storage device 130. The components of the image data management system 100 may be connected in one or more of various ways. Mere by way of example, as illustrated in FIG. 1, the imaging device 110 may be connected to the processing device 120 directly or through a network. As another example, the storage device 130 may be connected to the processing device 120 directly or through the network. As a further example, the imaging device 110 may be connected to the storage device 130 directly or through the network.

The imaging device 110 may be configured to acquire raw data relating to at least one part of a subject. The imaging device 110 may scan the subject or a portion thereof that is located within its detection region to acquire raw data of the subject or a portion thereof. In some embodiments, the imaging device 110 may include a single modality imaging device. For example, the imaging device 110 may include a digital subtraction angiography (DSA), a positron emission tomography (PET) device, a single-photon emission computed tomography (SPECT) device, a magnetic resonance imaging (MRI) device (also referred to as an MR device, an MR scanner), a computed tomography (CT) device (e.g., a micro CT device), an ultrasonography scanner, a digital radiography (DR) scanner, or the like, or any combination thereof. In some embodiments, the imaging device 110 may include a multi-modality imaging device. Exemplary multi-modality imaging devices may include a PET-CT device, a PET-MR device, or the like, or a combination thereof.

The processing device 120 may process data and/or information obtained from the imaging device 110 and/or the storage device 130. In some embodiments, the processing device 120 may be used to run one or more processes. For example, as illustrated in FIG. 1, the processing device 120 may run a first process 121, a second process 122, a third process 123, etc. The one or more processes may be software of the processing device 120. The processing device 120 may achieve functions of the processing device 120 by executing the one or more processes. For example, by running the first process 121, the processing device 120 may store raw data collected in a scan of a subject into the storage device 130 and generate first information relating to the raw data. As another example, by running the second process 122, the processing device 120 may obtain the first information from the first process 121 and store the first information into the storage device 130. As a further example, by performing the third process 123, the processing device 120 may obtain the first information from the second process 122; retrieve the raw data from the storage device 130 based on the first information, and reconstruct the retrieved raw data into a reconstruction image of the subject.

In some embodiments, each of the one or more processes may be executed by a corresponding process execution module. For example, the first process 121 may be executed by a first process execution module (e.g., a first process execution module 310 shown in FIG. 3), the second process 122 may be executed by a second process execution module (e.g., a second process execution module 320 shown in FIG. 3), the third process 123 may be executed by a third process execution module (e.g., a third process execution module 330 shown in FIG. 3).

In some embodiments, the processing device 120 may include a central processing unit (CPU), a digital signal processor (DSP), a system on a chip (SoC), a microcontroller unit (MCU), or the like, or any combination thereof. In some embodiments, the processing device 120 may include a computer, a user console, a single server or a server group, etc. The server group may be centralized or distributed. In some embodiments, the processing device 120 may be local or remote. For example, the processing device 120 may access information and/or data stored in the imaging device 110 and/or the storage device 130 via the network. As another example, the processing device 120 may be directly connected to the imaging device 110 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 or a portion of the processing device 120 may be integrated into the imaging device 110. In some embodiments, the processing device 120 may be implemented by a computing device 200 including one or more components as described in FIG. 2.

The storage device 130 may store data (e.g., the raw data, the first information, the reconstruction image), instructions, and/or any other information. In some embodiments, the storage device 130 may store data obtained from the imaging device 110 and/or the processing device 120. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. In some embodiments, the storage device 130 may be implemented on a cloud platform as described elsewhere in the disclosure.

In some embodiments, the storage device 130 may include multiple storage space used for storing different types of data. For example, as illustrated in FIG. 1, the storage device 130 may include first storage space 131, second storage space 132, and third storage space 133. Different storage space may correspond to different processes. For example, the first storage space 131 may correspond to the first process 121 and be used to store the raw data, the second storage space 132 may correspond to the second process 122 and be used to store the first information relating to the raw data, and the third storage space 133 may correspond to the third process 123 and be used to store the reconstruction image. In some embodiments, different storage space may be partitioned belonging to an independent same storage device (e.g., the storage device 130). Alternatively, different storage space may belong to different storage devices other than the storage device 130. For example, the first storage space 131 may belong to a solid state disk (SSD), the second storage space 132 may belong to a solid state disk (SSD) or a hard disk drive (HDD), and the third storage space 133 may belong to a hard disk drive (HDD). As another example, the first storage space 131 and the third storage space 133 may belong to a same or different removable storage device. In some embodiments, different storage space or different removable storage device may correspond to different processing devices. It should be noted that the storage device in the present disclosure refers to a physical storage device, and a storage space refers to a portion of the capacity of the physical storage device. For example, when the first storage space 131 and the third storage space 133 belong to an independent same storage device, the first storage space 131 and the third storage space 133 may correspond to different storage directories.

In some embodiments, the storage device 130 may be directly connected to or communicate with one or more components (e.g., the imaging device 110, the processing device 120) of the image data management system 100. One or more components of the image data management system 100 may access the data or instructions stored in the storage device 130. In some embodiments, the storage device 130 may be part of the imaging device 110 or the processing device 120.

It should be noted that the above description of the image data management system 100 is merely provided for the purposes of illustration, and not intended to limit the scope of the present disclosure. For persons having ordinary skills in the art, multiple variations and modifications may be made under the teachings of the present disclosure. For example, the image data management system 100 may include one or more additional components (e.g., a network, a terminal device) and/or one or more components of the image data management system 100 described above may be omitted. Additionally or alternatively, two or more components of the image data management system 100 may be integrated into a single component. A component of the image data management system 100 may be implemented on two or more sub-components. However, those variations and modifications do not depart from the scope of the present disclosure.

Figure 2:
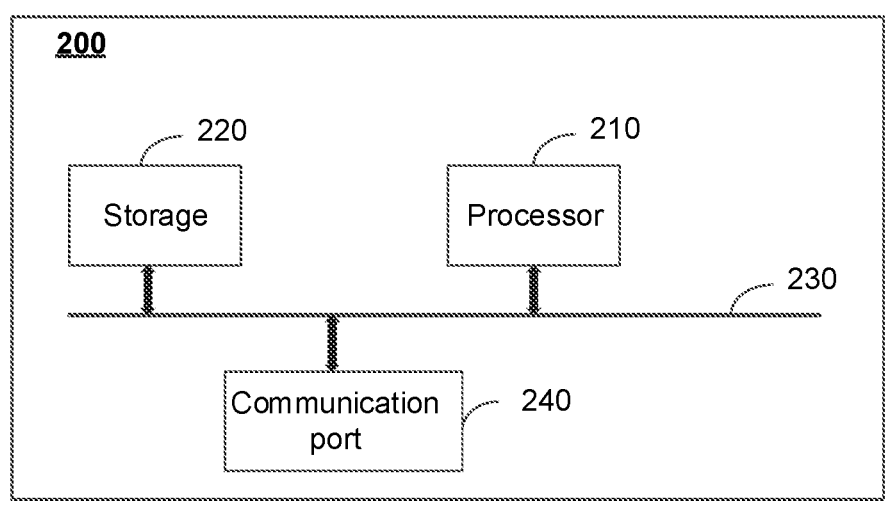
FIG. 2 is a schematic diagram illustrating exemplary hardware and/or software components of a computing device according to some embodiments of the present disclosure.

FIG. 2 is a schematic diagram illustrating exemplary hardware and/or software components of a computing device according to some embodiments of the present disclosure. The computing device 200 may be used to implement any component of the image data management system 100 as described herein. For example, the processing device 120 may be implemented on the computing device 200 via its hardware, software program, firmware, or a combination thereof. Although only one such computing device is shown, for convenience, the computer functions relating to the image data management system 100 as described herein may be implemented in a distributed fashion on a number of similar platforms, to distribute the processing load. As illustrated in FIG. 2, the computing device 200 may include a processor 210, a storage 220, a data bus 230, and a communication port 240.

The processor 210 may execute computer instructions (e.g., program codes) and perform functions of the processing device 120 in accordance with techniques described herein. The computer instructions may include, for example, threads, routines, programs, objects, components, data structures, procedures, modules, and functions, which perform particular functions described herein. For example, by running the first process 121, the processor 210 may store raw data collected in a scan of a subject into the first storage space 131 of the storage device 130 and generate first information relating to the raw data. As another example, by running the second process 122, the processor 210 may obtain the first information from the first process 121; store the first information into the second storage space 132 of the storage device 130; and reconstruct the raw data into a reconstruction image of the subject based on the first information stored in the second storage space 132.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the storage device 130, and/or any other component of the image data management system 100. In some embodiments, the storage 220 may include a mass storage device, a removable storage device, a volatile read-and-write memory, a read-only memory (ROM), or the like, or a combination thereof. In some embodiments, the storage 220 may store one or more programs and/or instructions to perform exemplary methods described in the present disclosure.

The data bus 230 may be configured to implement data communications among components of the computing device 200. In some embodiments, hardware in the computing device 200 may transmit data via the data bus 230. For example, the processor 210 may send data to the storage 220 or other hardware such as the communication port 240 via the data bus 230.

The communication port 240 may be connected to a network to facilitate data communications. The communication port 240 may establish connections between the processing device 120 and one or more components (e.g., the imaging device 110, the storage device 130) of the image data management system 100. The connection may be a wired connection, a wireless connection, any other communication connection that can enable data transmission and/or reception, and/or a combination of these connections.

It should be noted that the above description of the computing device 200 is merely provided for the purposes of illustration, and not intended to limit the scope of the present disclosure. For persons having ordinary skills in the art, multiple variations and modifications may be made under the teachings of the present disclosure. For example, the computing device 200 may include one or more additional components (e.g., an input/output) and/or one or more components of the computing device 200 described above may be omitted. Additionally or alternatively, two or more components of the computing device 200 may be integrated into a single component. A component of the computing device 200 may be implemented on two or more sub-components. However, those variations and modifications do not depart from the scope of the present disclosure.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the data storage as described herein. A computer with user interface elements may be used to implement a personal computer (PC) or another type of work station or terminal, although a computer may also act as a server if appropriately programmed. It is believed that those skilled in the art are familiar with the structure, programming and general operation of such computer equipment and as a result the drawings should be self-explanatory.

Figure 3:
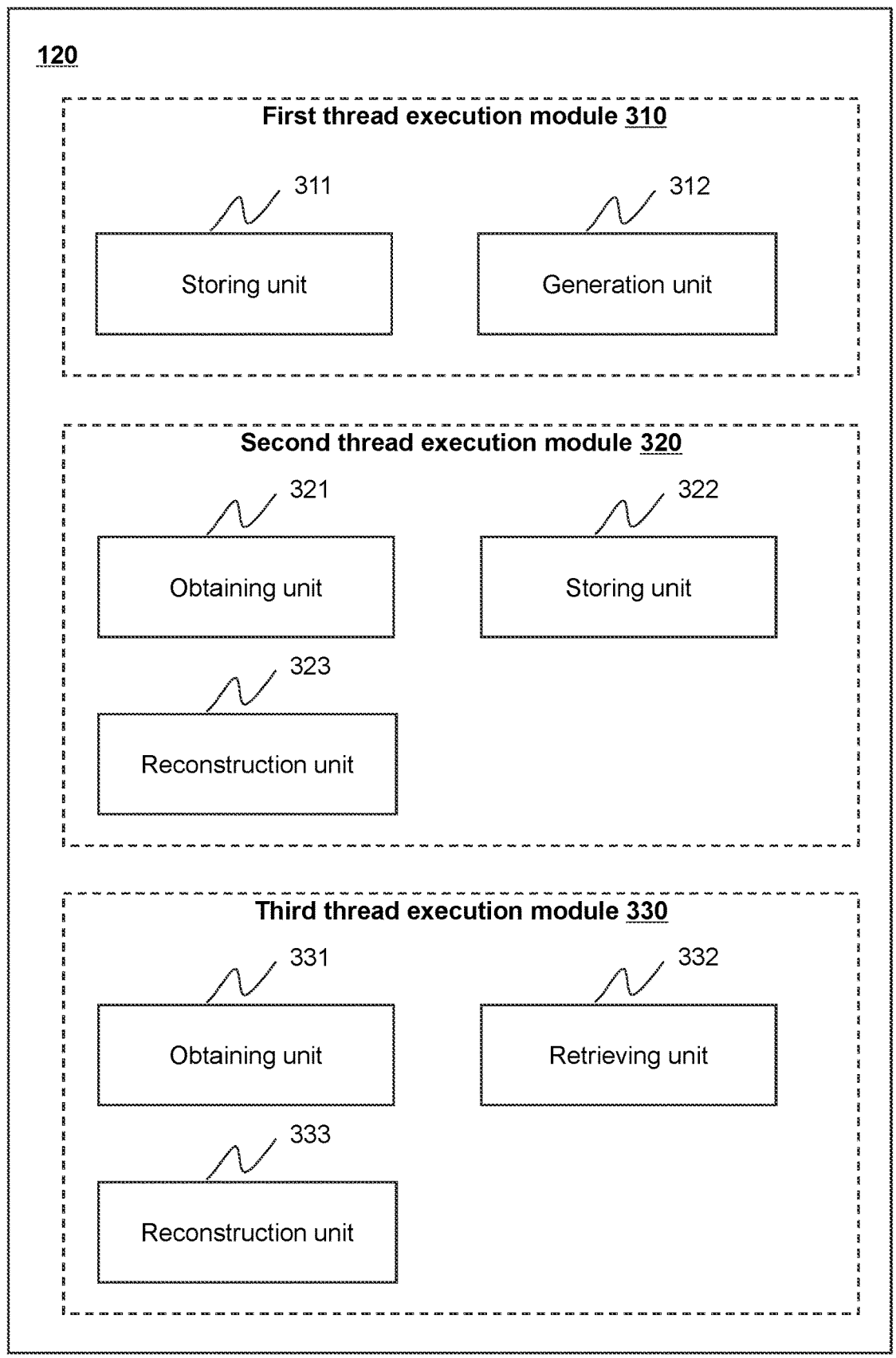
FIG. 3 is a block diagram illustrating an exemplary processing device according to some embodiments of the present disclosure.

FIG. 3 is a block diagram illustrating an exemplary processing device according to some embodiments of the present disclosure. The processing device 120 may be implemented on the computing device 200 (e.g., the processor 210) illustrated in FIG. 2. As illustrated in FIG. 3, the processing device 120 may include a first process execution module 310, a second process execution module 320, and a third process execution module 330.

The first process execution module 310 may be configured to execute a first process (e.g., the first process 121). In some embodiments, the first process execution module 310 may include a storing unit 311 and a generation unit 312.

In some embodiments, the storing unit 311 may be configured to store raw data collected in a scan of a subject into first storage space (e.g., the first storage space 131) of at least one storage device (e.g., the storage device 130, the storage 220). More descriptions may be found elsewhere in the present disclosure (e.g., operation 410 and the description thereof).

In some embodiments, the storing unit 311 may be configured to obtain raw data of a subject collected by an imaging device and determine whether the first storage space satisfies a condition. In response to determining that the first storage space does not satisfy the condition, the storing unit 311 may be configured to determine at least one target raw data set from historical raw data sets that have already been stored in the first storage space. For example, for each historical raw data set, the storing unit 311 may be configured to construct a feature vector representing the historical raw data set and determine an evaluation score of the historical raw data set by inputting the feature vector into a machine learning model. According to the evaluation score of each historical raw data set, the storing unit 311 may be configured to determine the at least one target raw data set from the historical raw data sets. Further, the storing unit 311 may be configured to delete or compress the at least one target raw data set stored in the first storage space. More descriptions may be found elsewhere in the present disclosure (e.g., FIG. 6 and the description thereof).

In some embodiments, the storing unit 311 may be configured to obtain a protection instruction for protecting the raw data from deletion or compression and copy, in response to the protection instruction, the raw data into storage space other than the first storage space for permanent storage.

In some embodiments, the generation unit 312 may be configured to generate first information relating to the raw data. More descriptions may be found elsewhere in the present disclosure (e.g., operation 420 and the description thereof).

In some embodiments, the generation unit 312 may be configured to delete the raw data.

In some embodiments, the generation unit 312 may be configured to determine whether each of the plurality of acquisition modules operates normally during data acquisition and delete, in response to determining that at least one of the plurality of acquisition modules does not operate normally during the data acquisition, the raw data stored in the first storage space.

In some embodiments, the generation unit 312 may be configured to obtain an association instruction with respect to the raw data and associate, in response to the association instruction, the raw data and other data relating to the raw data stored in the first storage space based on tag information of the raw data and the other data.

The second process execution module 320 may be configured to execute a second process (e.g., the second process 122). In some embodiments, the second process execution module 320 may include an obtaining unit 321, a storing unit 322, and a reconstruction unit 323.

In some embodiments, the obtaining unit 321 may be configured to obtain the first information from the first process (e.g., the first process 121). More descriptions may be found elsewhere in the present disclosure (e.g., operation 430 and the description thereof).

In some embodiments, the obtaining unit 321 may be configured to obtain the second information from the third process. More descriptions may be found elsewhere in the present disclosure (e.g., operation 510 and the description thereof).

In some embodiments, the storing unit 322 may be configured to store the first information into second storage space (e.g., the second storage space 132) of the at least one storage device (e.g., the storage device 130, the storage 220). More descriptions may be found elsewhere in the present disclosure (e.g., operation 440 and the description thereof).

In some embodiments, the storing unit 322 may be configured to store the second information. For example, the storing unit 322 may be configured to store the second information into the second storage space or other storage space (or storage devices). In some embodiments, the storing unit 322 may be configured to update the first information in the second storage space based on the second information. More descriptions may be found elsewhere in the present disclosure (e.g., operation 511 and the description thereof).

The third process execution module 330 may be configured to execute a third process (e.g., the third process 123). In some embodiments, the third process execution module 330 may include an obtaining unit 331, a retrieving unit 332, and a reconstruction unit 333.

In some embodiments, the obtaining unit 331 may be configured to obtain the first information from the second process. More descriptions may be found elsewhere in the present disclosure (e.g., operation 505 and the description thereof).

In some embodiments, the obtaining unit 331 may be configured to obtain a deletion instruction to delete the reconstruction image stored in the third storage space and the corresponding raw data stored in the first storage space and transmit, in response to the deletion instruction, the first information to the first process.

In some embodiments, the retrieving unit 332 may be configured to retrieve the raw data from the first storage space based on the first information. More descriptions may be found elsewhere in the present disclosure (e.g., operation 506 and the description thereof).

In some embodiments, the reconstruction unit 333 may be configured to reconstruct the retrieved raw data into the reconstruction image of the subject. More descriptions may be found elsewhere in the present disclosure (e.g., operation 507 and the description thereof).

In some embodiments, the reconstruction unit 333 may be configured to store the reconstruction image of the subject into third storage space (e.g., the third storage space 133) of the at least one storage device (e.g., the storage device 130). More descriptions may be found elsewhere in the present disclosure (e.g., operation 508 and the description thereof).

In some embodiments, the reconstruction unit 333 may be configured to generate second information relating to reconstruction image. More descriptions may be found elsewhere in the present disclosure (e.g., operation 509 and the description thereof).

In some embodiments, the reconstruction unit 333 may be configured to delete the reconstruction image.

It should be noted that the above description regarding the processing device 120 is merely provided for the purposes of illustration, and not intended to limit the scope of the present disclosure. For persons having ordinary skills in the art, multiple variations and modifications may be made under the teachings of the present disclosure. In some embodiments, two or more of the modules may be combined into a single module, and any one of the modules may be divided into two or more units. For example, the reconstruction unit 323 and the reconstruction unit 333 may be combined as a single module. However, those variations and modifications do not depart from the scope of the present disclosure.

Figure 4:
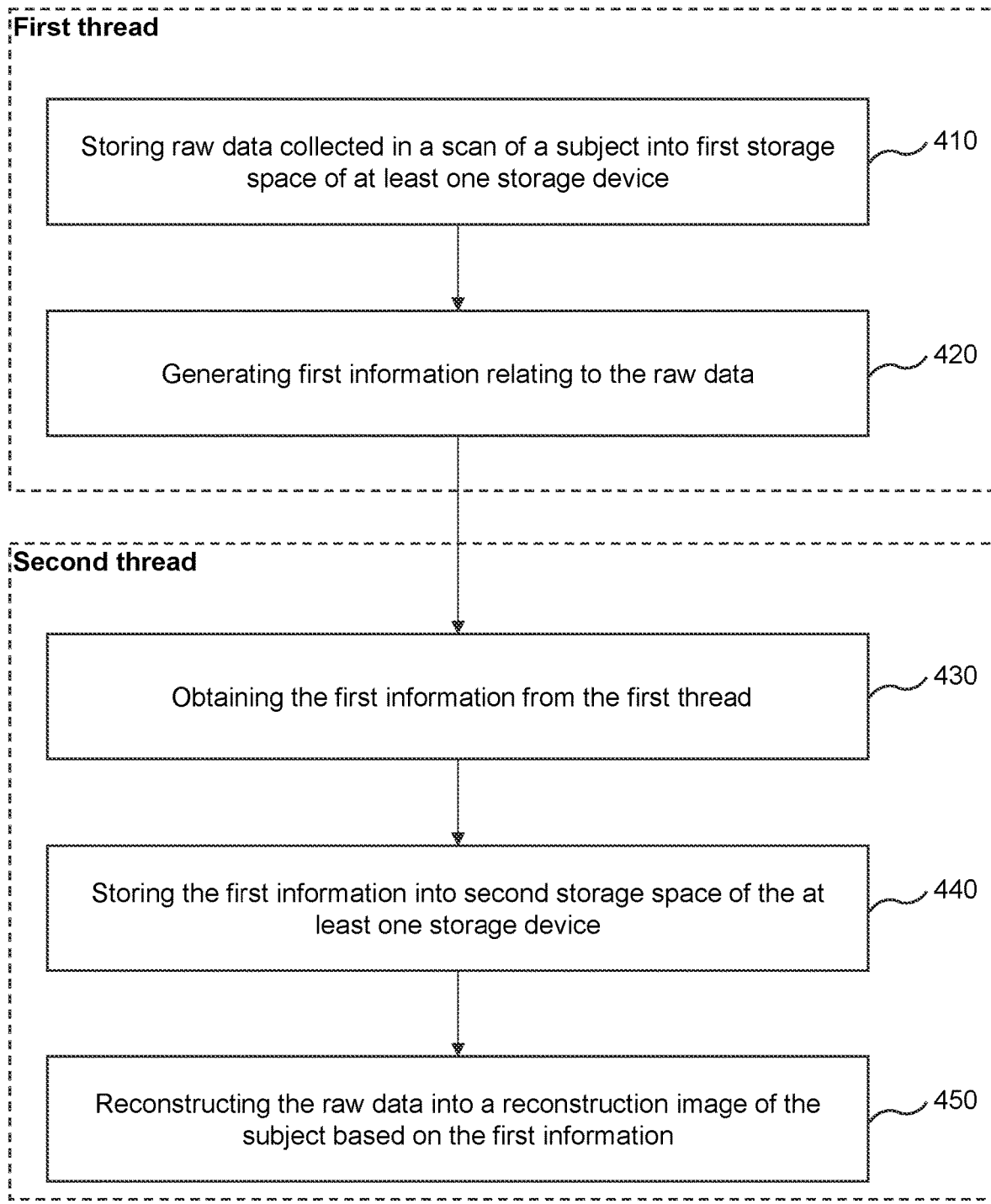
FIG. 4 is a flowchart illustrating an exemplary process for image data management according to some embodiments of the present disclosure.

FIG. 4 is a flowchart illustrating an exemplary process for image data management according to some embodiments of the present disclosure. In some embodiments, process 400 may be executed by the image data management system 100. For example, the process 400 may be implemented as a set of instructions (e.g., an application) stored in a storage device (e.g., the storage device 130, the storage 220). In some embodiments, the processing device 120 (e.g., the processor 210, and/or one or more modules of the processing device 120 illustrated in FIG. 3) may execute the set of instructions and may accordingly be directed to perform the process 400.

In 410, by running a first process (e.g., the first process 121), the processing device 120 (e.g., the storing unit 311 of the first process execution module 310) may store raw data collected in a scan of a subject into first storage space (e.g., the first storage space 131) of at least one storage device (e.g., the storage device 130, the storage 220).

The raw data may be original data collected in the scan of the subject. In some embodiments, the processing device 120 may direct or cause the imaging device 110 to perform a scan (e.g., an MR scan, a CT scan, a PET scan) on the subject to collect the raw data. In some embodiments, the subject may include a biological subject and/or a non-biological subject. The biological subject may be a human being (e.g., a patient), an animal, a plant, or a specific portion, organ, and/or tissue thereof. For example, the tissue may include epithelial tissue, connective tissue, muscle tissue, neural tissue, soft tissue, or the like, or any combination thereof. As another example, the organ may include heart, liver, spleen, lung, stomach, or the like, or any combination thereof. In some embodiments, the subject may be a man-made composition of organic and/or inorganic matters that are with or without life. In the present disclosure, the term "object" or "subject" are used interchangeably in the present disclosure. In some embodiments, the processing device 120 may monitor the operation status of the imaging device 110. Once the imaging device 110 finishes the scan, the processing device 120 may operate the first process.

In some embodiments, by running the first process, the processing device 120 may store the raw data by category. For example, the processing device 120 may store the raw data by category according to an energy level corresponding to the raw data. As another example, the processing device 120 may store the raw data by category based on a scientific research project to which the raw data belongs.

In some embodiments, before storing the raw data collected in the scan of the subject into the first storage space, the processing device 120 may run the first process to determine whether the first storage space satisfies a condition. In response to determining that the first storage space does not satisfy the condition, the processing device 120 may determine at least one target raw data set from historical raw data sets that have already been stored in the first storage space and delete or compress the at least one target raw data set stored in the first storage space. More descriptions regarding the deleting or compressing of the at least one target raw data set may be found elsewhere in the present disclosure (e.g., FIG. 6 and the description thereof).

Figure 7:
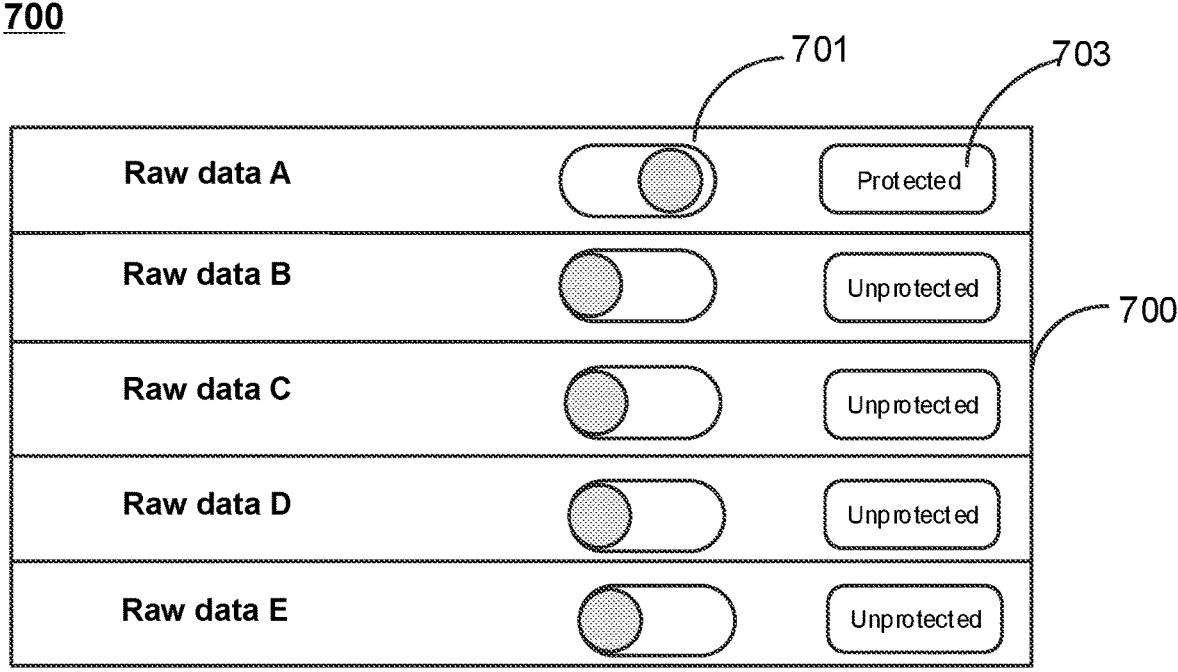
FIG. 7 is a schematic diagram illustrating an exemplary user interface according to some embodiments of the present disclosure.

In some embodiments, the processing device 120 may run the first process to obtain a protection instruction for protecting the raw data from deletion or compression. In response to the protection instruction, the processing device 120 may copy the raw data into storage space other than the first storage space for permanent storage. For example, a user may input the protection instruction by setting a protection label for raw data to be protected via a user interface (e.g., a user interface 700 as shown in FIG. 7). By running the first process, the processing device 120 may copy the raw data with the protection label to the storage space other than the first storage space connected or communicated with the processing device 120 for permanent storage. Merely by way of example, the storage space other than the first storage space may include a hard disk, a universal serial bus (USB) flash disk, an optical disk storage, etc. After the raw data with the protection label is stored in the storage space other than the first storage space, the processing device 120 may record and store storage information of the raw data with the protection label in the form of a database, a table, etc. The storage information may include a storage address, a type, an identification, etc. of the raw data with the protection label. In some embodiments, a certain amount of memory may be allocated in the at least one storage device for storing the raw data with the protection label.

In some embodiments, the user may not be able to delete the raw data with the protection label. If the user wants to delete the raw data with the protection label, he/she may need to input an instruction to cancel the protection label of the raw data via the user interface. After the protection label of the raw data is canceled, the user can delete the raw data.

By setting the protection label, raw data that needs to be protected may be backed up. In such cases, the protected raw data may be read from the storage space other than the first storage space even if the raw data stored in the first storage space is accidentally damaged or lost, which improves the storage security and reliability of the raw data.

In some embodiments, the processing device 120 may also store information of the subject and/or scanning parameters of the imaging device 110 into the first storage space. The scanning parameters may include an echo time, a repeat time, etc.

In a practical application, the processing device 120 may hierarchically store the raw data collected by the imaging device 110 and other data associated with the raw data in the first storage space. For example, the processing device 120 may store the raw data and the other data associated with the raw data according to a hierarchy of subject data—study data—series data—scan layer data in the first storage space. The subject data may refer to data related to the subject and may include such as a type (e.g., a cat), a weight, an identification, etc. of the subject. The study data may refer to data related to the scan of the subject and may include such as a scan serial number, a scan time, a scan part of the subject, etc. The series data may refer to data related to multiple scans of the subject and may include a layer thickness of each scan layer, a layer spacing of any two scan layers, etc., of each scan. The scan layer data may refer to data associated with each scan layer in each scan and may include a resolution, a pixel pitch, etc. of each layer scan.

Since a large amount of data can be stored in each hierarchy of the first storage space, if all data under one hierarchy needs to be deleted, tedious and complex operations may be required. Thus, in some embodiments of the present disclosure, the processing device 120 may associate all the data under a hierarchy of the first storage space, so that all the data under the same hierarchy may be deleted or updated at the same time.

Specifically, the processing device 120 may run the first process (e.g., the first process 121) to obtain an association instruction with respect to raw data. In response to the association instruction, the processing device 120 may associate the raw data and other data relating to the raw data stored in the first storage space based on tag information of the raw data and the other data. In some embodiments, the association instruction may include tag information of the raw data that needs to be associated with other data. After receiving the association instruction, the processing device 120 may obtain the tag information of the association instruction. The tag information may include hierarchy information (e.g., the study data, the series data, etc.) of the storage of the raw data that needs to be associated with other data. After obtaining the tag information, the processing device 120 may associate the raw data and other data whose tag information is the same or similar to the tag information of the raw data. For example, the processing device 120 may associate the raw data and other data with the same study identification (i.e., raw data that belong to the same study may be associated with each other). It should be noted that data obtained in the same data collection process have the same study identification.

By associating the raw data and other data with the same tag information, image data management may be more convenient and faster, thereby having improved efficiency.

In some embodiments, the raw data may include raw data subsets collected by a plurality of acquisition modules of the imaging device (e.g., the imaging device 110). The processing device 120 may run the first process (e.g., the first process 121) to determine whether each of the plurality of acquisition modules operates normally during data acquisition. In response to determining that at least one of the plurality of acquisition modules does not operate normally during the data acquisition, the processing device 120 may delete the raw data stored in the first storage space. More descriptions regarding the plurality of acquisition modules may be found elsewhere in the present disclosure (e.g., FIG. 8 and the description thereof).

In 420, by running the first process (e.g., the first process 121), the processing device 120 (e.g., the generation unit 312 of the first process execution module 310) may generate first information relating to the raw data.

The first information may refer to various information relating to the raw data. In some embodiments, the first information may include various information relating to the storage procedure of the raw data. For example, the first information may include an identification, a type, a size, and/or a storage address, an identification of a study or project that the raw data belongs to, etc. of the raw data. The storage address of the raw data may refer to data used to uniquely identify a storage position of the raw data in the first storage space. In some embodiments, the first information may include various abstract information relating to the raw data.

In 430, by running a second process (e.g., the second process 122), the processing device 120 (e.g., the obtaining unit 321 of the second process execution module 320) may obtain the first information from the first process (e.g., the first process 121).

In some embodiments, data may be exchanged between the first process and the second process, so that the processing device 120 may process the data collaboratively using the first process and the second process. For example, the first information may be sent from the first process to the second process, so that the second process may read required data (e.g., the raw data) from the first storage space according to the first information. In some embodiments, the first process and the second process may communicate with each other via, for example, a data exchange mode, a parallel bus mode, a serial bus mode, etc. The serial bus mode may include a single bus mode, a universal asynchronous receiver/transmitter (UART) mode, etc.

In 440, by running the second process (e.g., the second process 122), the processing device 120 (e.g., the storing unit 322 of the second process execution module 320) may store the first information into second storage space (e.g., the second storage space 132) of the at least one storage device (e.g., the storage device 130, the storage 220).

After obtaining the first information, the processing device 120 may store, by running the second process, the first information in the second storage space to facilitate recording and calling of the first information. The second storage space may be storage space different from (e.g., independent from) the first storage space. The first storage space may be used to store the raw data, while the second storage space may be used to store the first information relating to the raw data (e.g., the storage address of the raw data in the first storage space).

In 450, by running the second process (e.g., the second process 122), the processing device 120 (e.g., the reconstruction unit 323 of the second process execution module 320) may reconstruct the raw data into a reconstruction image of the subject based on the first information stored in the second storage space.

In some embodiments, by running the second process, the processing device 120 may obtain the raw data corresponding to the first information from the first storage space of the at least one storage device. For example, the processing device 120 may determine the storage address of the raw data in the first storage space of the at least one storage device according to the first information. Further, the processing device 120 may retrieve the raw data based on the storage address of the raw data.

In some embodiments, after obtaining the raw data corresponding to the first information, the processing device 120 may run the second process to reconstruct the raw data to generate a reconstruction image. The reconstruction image may include such as a CT image, an MRI image, a PET image, etc. A storage format of the reconstruction image may include a digital image correlation method (DICOM) format, an analysis format, a NIfTI format, etc. The reconstruction may refer to a process of generating a two-dimensional image or a three-dimensional image by processing complete or incomplete raw data using a reconstruction algorithm and/or a reconstruction parameter. The reconstruction algorithm may include, but is not limited to, a back projection reconstruction algorithm, an iterative reconstruction algorithm, an analytical reconstruction algorithm, etc. The analytical reconstruction algorithm may include such as a filter back projection reconstruction algorithm, a Fourier transform reconstruction algorithm, etc. The reconstruction parameter may include a reconstruction matrix, an image uniformity correction parameter, a reference window width, etc. In some embodiments, the processing device 120 may obtain the reconstruction algorithm and/or the reconstruction parameter set by a user in real time. In some embodiments, the reconstruction algorithm and/or the reconstruction parameter may be pre-stored in a preset parameter library or the at least one storage device (e.g., the storage device 130, the storage 220), and the processing device 120 may read the reconstruction algorithm and/or the reconstruction parameter from the preset parameter library or the at least one storage device.

Further, by running the second process, the processing device 120 may store the reconstruction image of the subject into third storage space of the at least one storage device and generate second information relating to the reconstruction image. Further, by running the second process, the processing device 120 may store the second information into second storage space of the at least one storage device.

In some embodiments, the processing device 120 may run a third process (e.g., the third process 123) to obtain the first information from the second process (or the second storage space of the at least one storage device), retrieve the raw data from the first storage space of the at least one storage device based on the first information, and reconstruct the retrieved raw data into the reconstruction image of the subject. Further, the processing device 120 may run the third process to store the reconstruction image of the subject into third storage space (e.g., the third storage space 133) of the at least one storage device and generate second information relating to the reconstruction image. Further, the processing device 120 may run the second process (e.g., the second process 122) to obtain the second information from the third process and store the second information. For example, the processing device 120 may store the second information into the second storage space or other storage space (or storage devices). More descriptions regarding the generation of the reconstruction image and the generation and storing of the second information may be found elsewhere in the present disclosure (e.g., FIG. 5 and the description thereof).

In the embodiments of the present disclosure, the processing device 120 may respectively manage the raw data, the storage information (e.g., the first information) of the raw data, the reconstruction image generated by the reconstruction of the raw data, and the storage information (e.g., the second information) of the reconstruction image using the different processes and storage space. For example, the processing device 120 may use the first process to obtain the raw data, store the raw data, and generate the first information; use the third process to reconstruct the raw data, store the reconstruction image, and generate the second information; use the second process to store the first information and the second information. As another example, the processing device 120 may store the raw data in the first storage space; store the first information and the second information in the second storage space, and store the reconstruction image in the third storage space. The three processes and the three storage space may be independent from each other and not interfere with each other, which improves a storage speed of the raw data, a speed of image reconstruction, and a storage speed of the reconstruction image, thereby improving the management efficiency of image data. Accordingly, when a process crashes, other processes may not be affected, which improves the fault tolerance rate of the data management system, reduces the mutual influence between different data in the storage process, improves the orderliness of the storage space, and facilitate data access.

It should be noted that the above description regarding the process 400 is merely provided for the purposes of illustration, and not intended to limit the scope of the present disclosure. For persons having ordinary skills in the art, multiple variations and modifications may be made under the teachings of the present disclosure. In some embodiments, the process 400 may be accomplished with one or more additional operations not described and/or without one or more of the operations discussed above. For example, the process 400 may include an additional transmitting operation in which the processing device 120 may transmit the raw data, the first information, the reconstruction image, and/or the second information to a terminal device. However, those variations and modifications do not depart from the scope of the present disclosure.

Figure 5:
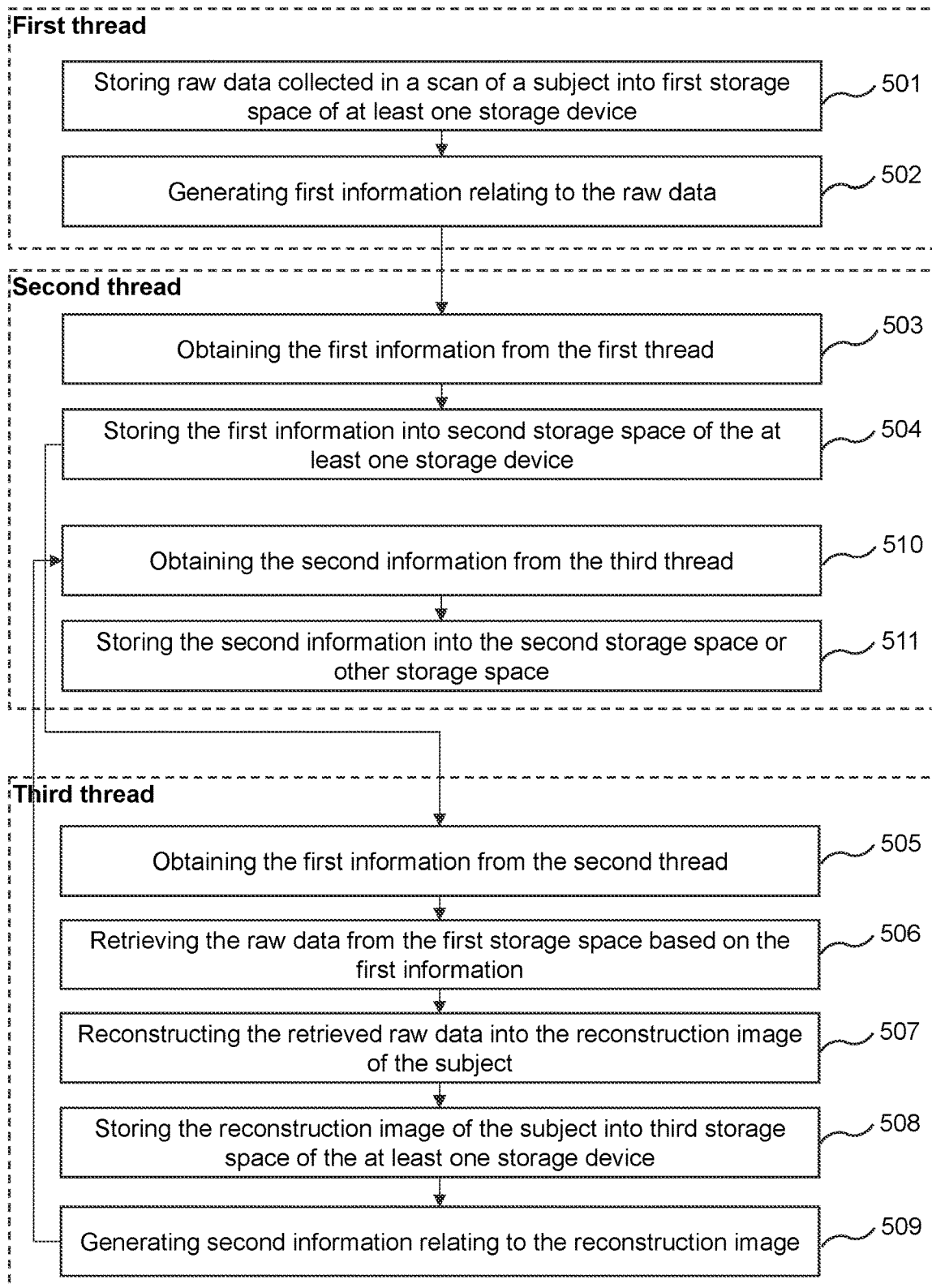
FIG. 5 is a flowchart illustrating an exemplary process for image data management according to some embodiments of the present disclosure.

FIG. 5 is a flowchart illustrating an exemplary process for image data management according to some embodiments of the present disclosure. In some embodiments, process 500 may be executed by the image data management system 100. For example, the process 500 may be implemented as a set of instructions (e.g., an application) stored in a storage device (e.g., the storage device 130, the storage 220). In some embodiments, the processing device 120 (e.g., the processor 210, and/or one or more modules of the processing device 120 illustrated in FIG. 3) may execute the set of instructions and may accordingly be directed to perform the process 500.

In 501, by running a first process (e.g., the first process 121), the processing device 120 (e.g., the storing unit 311 of the first process execution module 310) may store raw data collected in a scan of a subject into first storage space (e.g., the first storage space 131) of at least one storage device (e.g., the storage device 130). Operation 501 may be performed in a similar manner as operation 410, and the descriptions thereof are not repeated here.

In 502, by running the first process (e.g., the first process 121), the processing device 120 (e.g., the generation unit 312 of the first process execution module 310) may generate first information relating to the raw data. Operation 502 may be performed in a similar manner as operation 420, and the descriptions thereof are not repeated here.

In 503, by running a second process (e.g., the second process 122), the processing device 120 (e.g., the obtaining unit 321 of the second process execution module 320) may obtain the first information from the first process. Operation 503 may be performed in a similar manner as operation 430, and the descriptions thereof are not repeated here.

In 504, by running the second process (e.g., the second process 122), the processing device 120 (e.g., the storing unit 322 of the second process execution module 320) may store the first information into second storage space of the at least one storage device. Operation 504 may be performed in a similar manner as operation 440, and the descriptions thereof are not repeated here.

In 505, by performing a third process (e.g., the third process 123), the processing device 120 (e.g., the obtaining unit 331 of the third process execution module 330) may obtain the first information from the second process.

In some embodiments, data may be exchanged between the second process and the third process, so that the processing device 120 may process the data collaboratively using the second process and the third process. For example, the first information may be sent from the second process to the third process, so that the third process may read required data (e.g., the raw data) from the first storage space according to the first information. In some embodiments, the first process and the third process may communicate with each other via, for example, a data exchange mode, a parallel bus mode, a serial bus mode, etc. The serial bus mode may include a single-bus mode, a UART mode, etc.

In some embodiments, by performing the third process (e.g., the third process 123), the processing device 120 may obtain the first information from the second storage space (e.g., the second storage space 132) of the at least one storage device (e.g., the storage device 130, the storage 220).

In 506, by performing the third process (e.g., the third process 123), the processing device 120 (e.g., the retrieving unit 332 of the third process execution module 330) may retrieve the raw data from the first storage space based on the first information.

For example, the processing device 120 may retrieve the raw data from the first storage space based on the storage address of raw data.

In 507, by performing the third process (e.g., the third process 123), the processing device 120 (e.g., the reconstruction unit 333 of the third process execution module 330) may reconstruct the retrieved raw data into the reconstruction image of the subject. The reconstruction of the retrieved raw data may be performed in a similar manner as that described in connection with operation 450, and the descriptions thereof are not repeated here.

In 508, by performing the third process (e.g., the third process 123), the processing device 120 (e.g., the reconstruction unit 333 of the third process execution module 330) may store the reconstruction image of the subject into third storage space (e.g., the third storage space 133) of the at least one storage device (e.g., the storage device 130).

In 509, by performing the third process (e.g., the third process 123), the processing device 120 (e.g., the reconstruction unit 333 of the third process execution module 330) may generate second information relating to the reconstruction image.

The second information may refer to various information relating to the reconstruction image. In some embodiments, the second information may include various information relating to a storage procedure of the reconstruction image. For example, the second information may include an identification, a type, a size, and/or a storage address of the reconstruction image. The storage address of the reconstruction image may refer to data used to uniquely identify a storage position of the reconstruction image in the third storage space. In some embodiments, the second information may include abstract information relating to the reconstruction image. In some embodiments, the second information may also include information relating to the raw data corresponding to the reconstruction image (i.e., the raw data from which the reconstruction image is reconstructed). For example, the second information may include an identification of the raw data, an identification of a study or project that the raw data belongs to, or the like, or any combination thereof.

In 510, by running the second process (e.g., the second process 122), the processing device 120 (e.g., the obtaining unit 321 of the second process execution module 320) may obtain the second information from the third process.

In some embodiments, the second information may be sent from the third process to the second process, so that the second process may read required data (e.g., the reconstruction image) from the third storage space according to the second information. In some embodiments, by running the second process (e.g., the second process 122), the processing device 120 may obtain the second information from the third storage space (e.g., the third storage space 133) of the at least one storage device.

In 511, by running the second process (e.g., the second process 122), the processing device 120 (e.g., the storing unit 322 of the second process execution module 320) may store the second information. For example, the processing device 120 may store the second information into the second storage space or other storage space (or storage devices).

In some embodiments, the processing device 120 may run the second process (e.g., the second process 122) to update the first information in the second storage space based on the second information. For example, the processing device 120 may update the first information by adding at least part of the second information to the first information. Merely by way of example, the first information may include the identification and the storage address of the raw data, and the second information may include the identification of the raw data corresponding to the reconstruction image and the storage address of the reconstruction image. The processing device 120 may retrieve the first information that includes the same identification of the raw data as the second information, and add the storage address of the reconstruction image into the first information. In such cases, the updated first information may include both the storage address of the raw data in the first storage space and the storage address of the corresponding reconstruction image in the third storage space.

As another example, the processing device 120 may update the first information by associating the first information with the second information. Merely by way of example, association information between the first information and the second information that correspond to the same set of raw data may be generated, and the processing device 120 may update the first information by adding the association information into the first information. In such cases, the updated information may include the storage address of the raw data and the association information.

By updating the first information based on the second information, the first information relating to the storage of the raw data and the second information relating to a reconstruction image of the raw data may be associated with each other, thereby facilitating the access of the raw data and the reconstruction image corresponding to the raw data.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, a user may manage the raw data stored in the first storage space and/or the third reconstruction image stored in the third storage space through the image data management system 100. For example, the user may delete the raw data and/or the third reconstruction image through the image data management system 100.

In some embodiments, the user or the processing device 120 may determine whether to perform an association processing on the reconstruction image and the raw data corresponding to the reconstruction image according to an actual need. The association processing may include at least one of synchronous deletion, synchronous compression, or synchronous transmission. As used herein, synchronous deletion refers to deleting the reconstruction image and the raw data synchronously, synchronous compression refers to compressing the reconstruction image and the raw data synchronously, and synchronous transmission refers to transmitting the reconstruction image and the raw data synchronously.

In some embodiments, the processing device 120 may obtain a deletion instruction (or a compress instruction, or a transmitting instruction). For example, the user may input the deletion instruction, or the compress instruction, or the transmitting instruction through a user interface (UI) of a user terminal. The user terminal may transmit the deletion instruction, or the compression instruction, or the transmitting instruction to the processing device 120. In some embodiments, the user interface may include, but is not limited to, a command interface, a program interface, a menu interface, a graphic interface, etc.

In some embodiments, in response to the obtaining of the deletion instruction (or the compress instruction, or the transmitting instruction), the processing device 120 may delete (or compress, or transmit) the reconstruction image and the corresponding raw data synchronously or delete (or compress, or transmit) only the reconstruction image. In some embodiments, the deletion instruction (or the compress instruction, or the transmitting instruction) may include information relating to a scanning sequence associated with the collecting of the raw data. In some embodiments, the deletion instruction (or the compress instruction, or the transmitting instruction) may further include whether to delete (or compress, or transmit) the reconstruction image and the raw data synchronously. In some embodiments, whether to delete (or compress, or transmit) the reconstruction image and the raw data synchronously may be determined (or selected) by the user through the user interface (UI) of the user terminal. The processing device 120 may delete (or compress) the reconstruction image and the raw data based on the information in the deletion instruction. For example, when the deletion instruction (or the compress instruction, or the transmitting instruction) includes synchronous deletion (or synchronous compression, or synchronous transmission) of the reconstruction image and the raw data, the processing device 120 may retrieve the reconstruction image and the raw data based on the scanning sequence associated with the collecting of the raw data and delete (or compress, or transmit) the retrieved reconstruction image and raw data. Through the association processing of the reconstruction image and the raw data corresponding to the reconstruction image, the reconstruction image and the raw data corresponding to the reconstruction image may be processed synchronously, which improves the efficiency of image data management. As another example, when the deletion instruction (or the compress instruction, or the transmitting instruction) does not include synchronous deletion (or synchronous compression, or synchronous transmission) of the reconstruction image and the raw data, the processing device 120 may retrieve the reconstruction image based on the scanning sequence in the deletion instruction and delete (or compress, or transmit) the retrieved reconstruction image.

In some embodiments, the user may select (or determine) to delete (or compress, or transmit) the reconstruction image and the corresponding raw data synchronously or delete (or compress, or transmit) only the reconstruction image through the user interface (UI) of the user terminal. For example, there may be an association component (e.g., an icon, a button) on the user interface, when the user clicks or touches the association component, the processing device 120 may synchronously delete (or compress) the reconstruction image and the corresponding raw data. When the user does not click or touch the association component, the processing device 120 may delete (or compress) only the reconstruction image.

Figure 6:
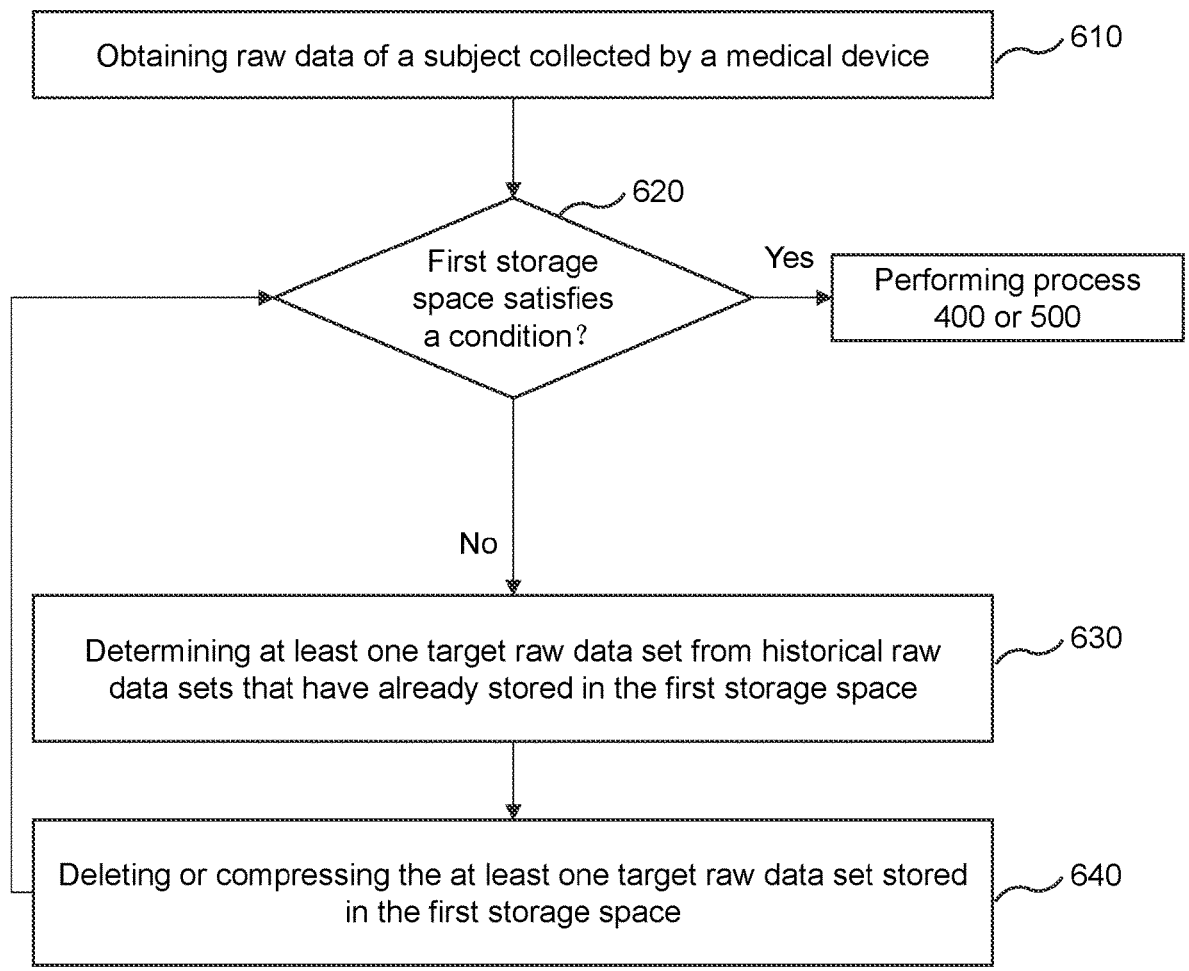
FIG. 6 is a flowchart illustrating an exemplary process for image data management according to some embodiments of the present disclosure.

FIG. 6 is a flowchart illustrating an exemplary process for image data management according to some embodiments of the present disclosure. In some embodiments, process 600 may be executed by the image data management system 100. For example, the process 600 may be implemented as a set of instructions (e.g., an application) stored in a storage device (e.g., the storage device 130, the storage 220). In some embodiments, the processing device 120 (e.g., the processor 210, and/or one or more modules of the processing device 120 illustrated in FIG. 3) may execute the set of instructions and may accordingly be directed to perform the process 600. In some embodiments, the process 600 may be performed before process 400 or 500.

In 610, the processing device 120 (e.g., the storing unit 311 of the first process execution module 310) may obtain raw data of a subject collected by an imaging device.

The raw data may need to be stored in first storage space (e.g., the first storage space 131) of at least one storage device (e.g., the storage device 130, the storage 220). In some embodiments, the processing device 120 may obtain the raw data by directing or causing the imaging device 110 to perform a scan (e.g., an MR scan, a CT scan, a PET scan) on the subject. In some embodiments, the raw data of the subject may be previously determined and stored in other storage space (e.g., an external storage device). The processing device 120 may obtain the raw data of the subject from the other storage space via a network.

In 620, the processing device 120 (e.g., the storing unit 311 of the first process execution module 310) may determine whether the first storage space satisfies a condition.

In some embodiments, the processing device 120 may determine whether unoccupied storage space in the first storage space is greater than or equal to a size of the raw data. If the unoccupied storage space in the first storage space is greater than or equal to the size of the raw data, the processing device 120 may determine that the first storage space satisfies the condition and perform process 400 or 500. If the unoccupied storage space in the first storage space is smaller than the size of the raw data, the processing device 120 may determine the first storage space does not satisfy the condition and perform operation 630.

In 630, the processing device 120 (e.g., the storing unit 311 of the first process execution module 310) may determine at least one target raw data set from historical raw data sets that have already been stored in the first storage space.

The at least one target raw data set may include one or more historical raw data sets that have relatively low importance and can be deleted or compressed. The importance of a historical raw data set may be determined based on various factors including, for example, whether the historical raw data set has a copy in other storage space, whether the historical raw data set has a protection label, the usage frequency of the historical raw data set, the quality of the historical raw data set, the storage time of the historical raw data set, a priority of the study or project that the historical raw data set belongs to, or the like, or any combination thereof.

Merely by way of example, for each historical raw data set, the processing device 120 may determine whether the historical raw data set is stored in storage space other than the first storage space or whether the historical raw data set has a protection label. If the historical raw data set is not stored in the storage space other than the first storage space or the historical raw data set has no protection label, the processing device 120 may designate the historical raw data set as a target raw data set.

As another example, for each historical raw data set, the processing device 120 may determine whether the historical raw data set has ever been used. If the historical raw data set has not ever been used, the processing device 120 may designate the historical raw data set as a target raw data set.

As yet another example, for each historical raw data set, the processing device 120 may determine whether an imaging device or an acquisition module of the imaging device collecting the historical raw data set operates normally during data acquisition of the historical raw data set. If the imaging device or the acquisition module of the imaging device collecting the historical raw data set does not operate normally during the data acquisition of the historical raw data, the processing device 120 may designate the historical raw data set as a target raw data set.

As yet another example, each time when a raw data set is collected by an imaging device, the processing device 120 may determine whether an amount of the raw data set is close to an expected amount. If a difference between the amount of the raw data set and the expected amount exceeds a preset threshold, the processing device 120 may label the raw data set as incomplete. For each historical raw data set, the processing device 120 may determine whether the historical raw data set is labeled as incomplete. If the historical raw data set is labeled as incomplete, the processing device 120 may designate the historical raw data set as a target raw data set.

As yet another example, the processing device 120 may designate a historical raw data set that belongs to a study or project with a low priority among the historical raw data sets as a target raw data set.

As yet another example, the processing device 120 may designate a historical raw data set that has been stored for a relatively long time among the historical raw data sets as a target raw data set.

In some embodiments, the processing device 120 may determine the at least one target raw data set from the historical raw data sets that have already been stored in the first storage space using a machine learning model. Specifically, for each historical raw data set, the processing device 120 may construct a feature vector representing the historical raw data set. Merely by way of example, elements of the feature vector may include a storage time of the historical raw data set, whether the historical raw data set has a protection label, a size of the historical raw data set, whether the historical raw data set is complete, whether the historical raw data set has ever been used, a priority of the study or project that the historical raw data set belongs to, or the like, or any combination thereof. An exemplary feature vector of a historical raw data set is represented as follows:

$$M=|300,0,150,1,1,2|$$

where M refers to the feature vector of the historical raw data set, 300 refers to that the historical raw data set has been stored in the first storage space for 300 days, 0 refers to that the historical raw data set does not have a protection label, 150 refers to the size of the historical raw data set is 150G, 1 refers to that the historical raw data set is complete, 1 refers to a count of times the historical raw data set has been used, and 2 refers to the priority of the study or project that the historical raw data set belongs to.

The processing device 120 may determine an evaluation score of each historical raw data set by inputting the feature vector of the historical raw data set into the machine learning model. The evaluation score may indicate the importance of the historical raw data set. For example, a historical raw data set with a higher evaluation score may have a lower importance. In some embodiments, the machine learning model may be pre-trained and stored in a storage device (e.g., the storage device 130, the storage 220) disclosed elsewhere in the present disclosure and/or an external storage device. The processing device 120 may retrieve the machine learning model from the storage device and/or the external storage device. In some embodiments, the machine learning model may include a neural network model. Merely by way of example, the neural network model may include a convolutional neural network (CNN), a fully convolutional neural network (FCN), a recursive Neural network (RNN)), a feedforward neural network (FNN), a recurrent neural network (RNN), a long and short-term memory neural network (LSTM), or the like, or any combination thereof. In some embodiments, the processing device 120 or another computing device may train the machine learning model based on a plurality of training samples online or offline. Each of the plurality of training samples may include a feature vector of a sample raw data set (as a training input) and a ground truth evaluation score of the sample raw data set (as a training label). The ground truth evaluation score of the sample raw data set may be determined by manual scoring, or according to a historical behavior of manually deleting or compressing the sample raw data set. For example, if a certain sample data set is manually deleted once within a one-year period, the sample data set may be assigned a high evaluation score.

Further, the processing device 120 may determine the at least one target raw data set from the historical raw data sets based on the evaluation score of each historical raw data set. For example, the processing device 120 may determine one or more historical raw data sets with a largest evaluation score in the historical raw data sets as the at least one target raw data set. In some embodiments, the processing device 120 may sort the historical raw data sets according to the evaluation scores of the historical raw data sets and display a ranking result of the historical raw data to a user via a terminal device, and the user may manually select the at least one target raw data set from the historical raw data sets.

In some embodiments, the count of the at least one target raw data set may be determined based on the size of the raw data. For example, a certain number of target raw data sets may be determined such that the remaining storage space in the first storage space after the target raw data sets are deleted or compressed is greater than the size of the raw data.

In 640, the processing device 120 (e.g., the storing unit 311 of the first process execution module 310) may delete or compress the at least one target raw data set stored in the first storage space.

In some embodiments, the processing device 120 may operate the first process to delete or compress the at least one target raw data set. Optionally, reconstruction image(s) corresponding to the at least one target raw data set may be deleted or compressed synchronously.

In some embodiments, after deleting (or compressing) the at least one target raw data set stored in the first storage space, the processing device 120 may perform operation 620 again to confirm whether the first storage space after the deletion or compression of the at least one target raw data set satisfies the condition. If the condition is not satisfied, operations 630 and 640 may be performed again until the first storage space satisfies the condition.

In the embodiments of the present disclosure, through the process 600, enough storage space may be automatically reserved for the storage of the raw data. In addition, the use of the machine learning model improves the intelligence of storage space management.

FIG. 7 is a schematic diagram illustrating an exemplary user interface 700 according to some embodiments of the present disclosure.

As shown in FIG. 7, the user interface 700 displays an interface element 701 and an interface element 703 corresponding to each set of raw data, wherein the interface element 701 is used to add a protection label to a set of raw data, and the interface element 703 is used to display the protection status of whether a set of raw data is protected. For example, the user interface 701 of raw data A is turned on, and thus the raw data A is assigned a projection label.

In some embodiments, when the user adds a protection label to a set of raw data, the processing device 120 may confirm an identity of the user through, for example, facial recognition, IP recognition, fingerprint recognition, account identification, terminal scanning code recognition, etc., so as to improve data security and avoid problems such as data leakage, data tampering, etc.

Figure 8:
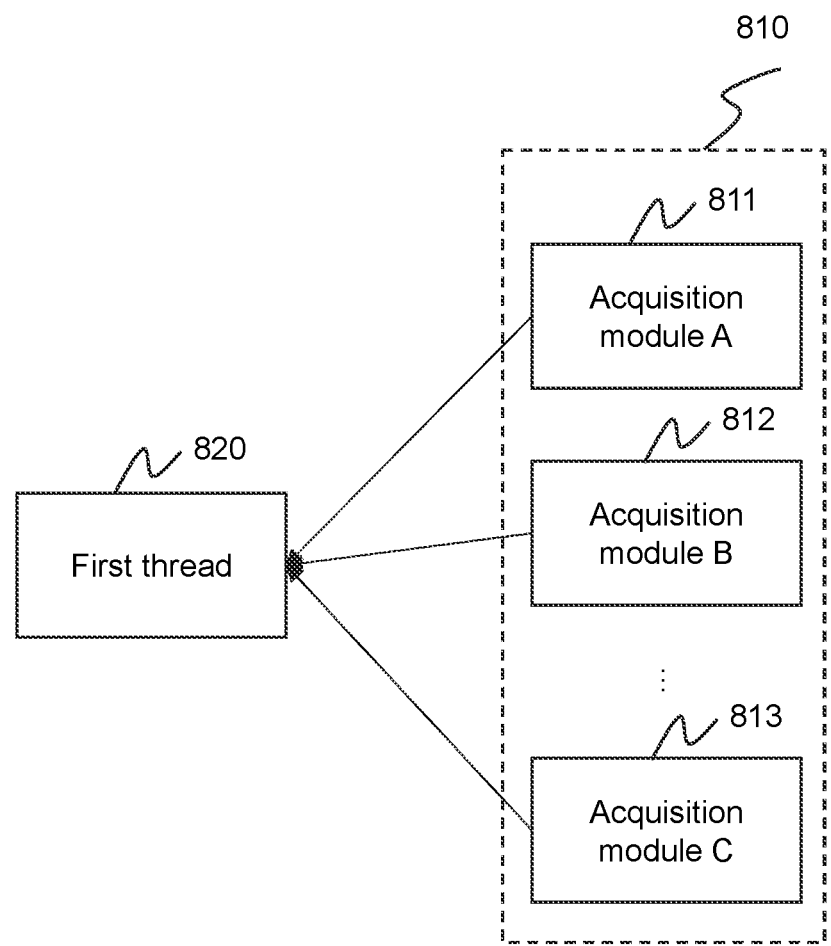
FIG. 8 is a schematic diagram illustrating exemplary acquisition modules of an imaging device according to some embodiments of the present disclosure.

FIG. 8 is a schematic diagram illustrating exemplary acquisition modules of an imaging device according to some embodiments of the present disclosure.

In some embodiments, raw data may include raw data subsets collected by a plurality of acquisition modules of an imaging device (e.g., the imaging device 110). The processing device 120 may manage the raw data subsets collected by the plurality of acquisition modules through the first process. The processing device 120 may connect the plurality of acquisition modules through the first process to receive the raw data subsets collected by the plurality of acquisition modules. For example, as shown in FIG. 8, the processing device 120 may be connected to an acquisition module 811, an acquisition module 812, and an acquisition module 813 of an imaging device 810 through a first process 820.

In some embodiments, an acquisition module (e.g., the acquisition module 811, the acquisition module 812, the acquisition module 813) may be an electronic device with capabilities of image acquisition and data transmission. Different acquisition modules may operate independently and not affect each other. For example, the acquisition module may include a CT device, a PET device, an MRI device, an ultrasound imaging device, etc. As another example, the acquisition module may be a detector of a CT device or a PET device. As yet another example, the acquisition module may be an MR coil of an MRI device.

If one or more of the plurality of acquisition modules do not operate normally during data acquisition, the raw data subsets collected by the abnormal acquisition module(s) and other normal acquisition modules cannot be used to reconstruct an image. Therefore, by running the first process, the processing device 120 may determine whether each of the plurality of acquisition modules operates normally during data acquisition. In response to determining that at least one of the plurality of acquisition modules does not operate normally during the data acquisition, the processing device 120 may delete the raw data stored in the first storage space. In some embodiments, the monitoring of the acquisition modules and the storage and management of the raw data may be performed continuously or intermittently (e.g., periodically) during the scan of the subject. For example, the raw data sets collected by the acquisition modules may be transmitted to the processing device 120 for storage in real-time during the scan. If the processing device 120 detects that one of the acquisition modules fails at a certain time, the raw data sets currently acquired by the acquisition modules and raw data sets that have been stored in the first storage space may be deleted. This can ensure that raw data stored by the processing device 120 is collected by the plurality of acquisition modules during a same running period, thereby improving the consistency and completeness of the raw data stored by the processing device 120.

The operations of the illustrated processes 400, 500, and 600 presented above are intended to be illustrative. In some embodiments, a process may be accomplished with one or more additional operations not described, and/or without one or more of the operations discussed. Additionally, the order in which the operations of a process described above is not intended to be limiting.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" may mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computing device including at least one processor and at least one storage device, the method comprising:
    by running a first process, storing raw data collected in a scan of a subject into first storage space of the at least one storage device; and generating first information relating to the raw data;
    by running a second process, obtaining the first information from the first process; and storing the first information into second storage space of the at least one storage device;
    reconstructing the raw data into a reconstruction image of the subject based on the first information; and
    performing an association processing of the reconstruction image and the raw data corresponding to the reconstruction image.

2. The method of claim 1, wherein the reconstructing the raw data into a reconstruction image of the subject based on the first information includes:
    by running the second process,
        retrieving the raw data from the first storage space based on the first information;
        reconstructing the retrieved raw data into the reconstruction image of the subject;
        storing the reconstruction image of the subject into third storage space of the at least one storage device;
        generating second information relating to the reconstruction image; and
        storing the second information into the second storage space of the at least one storage device.

3. The method of claim 1, wherein the reconstructing the raw data into a reconstruction image of the subject based on the first information includes:
    by performing a third process,
        obtaining the first information from the second process;
        retrieving the raw data from the first storage space based on the first information; and
        reconstructing the retrieved raw data into the reconstruction image of the subject.

4. The method of claim 3, wherein the method further includes:
    by performing the third process, storing the reconstruction image of the subject into third storage space of the at least one storage device; and generating second information relating to the reconstruction image; and
    by running the second process, obtaining the second information from the third process; and storing the second information.

5. The method of claim 4, wherein the storing the second information includes:
    updating the first information in the second storage space based on the second information.

6. The method of claim 1, wherein before storing the raw data collected in the scan of the subject into the first storage space, the method further includes:
    determining whether the first storage space satisfies a condition;
    in response to determining that the first storage space does not satisfy the condition, determining at least one target raw data set from historical raw data sets that have already been stored in the first storage space; and
    deleting or compressing the at least one target raw data set stored in the first storage space.

7. The method of claim 6, wherein the determining the at least one target raw data set from historical raw data sets that have already been stored in the first storage space includes:
    for each historical raw data set, constructing a feature vector representing the historical raw data set; and determining an evaluation score of the historical raw data set by inputting the feature vector into a machine learning model; and
    determining the at least one target raw data set from the historical raw data sets based on the evaluation score of each historical raw data set.

8. The method of claim 1, wherein the method further includes:
    by running the first process,
        obtaining a protection instruction for protecting the raw data from deletion or compression; and
        in response to the protection instruction, copying the raw data into storage space other than the first storage space for permanent storage.

9. The method of claim 1, wherein the method further includes:
    obtaining an association instruction with respect to the raw data; and
    in response to the association instruction, associating the raw data and other data relating to the raw data stored in the first storage space based on tag information of the raw data and the other data.

10. The method of claim 1, wherein the raw data includes raw data subsets collected by a plurality of acquisition modules of an imaging device, the method further includes:
    by running the first process,
        determining whether each of the plurality of acquisition modules operates normally during data acquisition; and
        in response to determining that at least one of the plurality of acquisition modules does not operate normally during the data acquisition, deleting the raw data stored in the first storage space.

11. The method of claim 1, wherein the method further includes:
    displaying a protection status of whether a set of raw data is protected on a user interface.

12. An imaging system, comprising:
    an imaging device configured to scan a subject;
    at least one storage device including a set of instructions; and
    at least one processor in communication with the at least one storage device, wherein when executing the set of instructions, the at least one processor causes the system to perform operations including:
       by running a first process, storing raw data collected in the scan of the subject into first storage space of the at least one storage device; and generating first information relating to the raw data;
       by running a second process, obtaining the first information from the first process; and storing the first information into second storage space of the at least one storage device;
       reconstructing the raw data into a reconstruction image of the subject based on the first information; and
       performing an association processing of the reconstruction image and the raw data corresponding to the reconstruction image.

13. A non-transitory computer readable medium, comprising executable instructions that, when executed by at least one processor, direct the at least one processor to perform a method, the method comprising:
    by running a first process, storing raw data collected in a scan of a subject into first storage space of the at least one storage device; and generating first information relating to the raw data;
    by running a second process, obtaining the first information from the first process; storing the first information into second storage space of the at least one storage device; and reconstructing the raw data into a reconstruction image of the subject based on the first information stored in the second storage space; and
    performing an association processing of the reconstruction image and the raw data corresponding to the reconstruction image.

14. The method of claim 1, wherein the association processing includes at least one of synchronous deletion, synchronous compression, or synchronous transmission, the synchronous deletion refers to deleting the reconstruction image and the raw data corresponding to the reconstruction image synchronously, the synchronous compression refers to compressing the reconstruction image and the raw data corresponding to the reconstruction image synchronously, and the synchronous transmission refers to transmitting the reconstruction image and the raw data corresponding to the reconstruction image synchronously.

15. The method of claim 14, wherein an association component is provided on a user interface communicatively connected to the computing device, and the performing an association processing includes:
    in response to that a user clicks or touches the association component, performing the association processing of the reconstruction image and the raw data corresponding to the reconstruction image.

16. The method of claim 15, wherein the method includes:
    in response to that the user does not click or touch the association component, performing a processing only on the reconstruction image, wherein the processing includes at least one of deletion, compression, or transmission.

17. The method of claim 14, wherein the performing an association processing on the reconstruction image and the raw data includes:
    obtaining information relating to a scanning sequence associated with the collecting of the raw data;
    retrieving the reconstruction image and the raw data based on the scanning sequence; and
    performing the association processing on the retrieved reconstruction image and the retrieved raw data.

18. The method of claim 1, wherein the first information includes at least one of an identification of the raw data, a type of the raw data, a size of the raw data, or a storage address of the raw data in the first storage space, an identification of a study or project that the raw data belongs to.

19. The method of claim 18, wherein the second storage space is a storage space different from the first storage space.

20. The method of claim 9, wherein the associating the raw data and other data includes:
    associating the raw data and the other data whose tag information is the same as the tag information of the raw data.

* * * * *